United States Patent [19]
Llyod et al.

[11] Patent Number: 5,328,455
[45] Date of Patent: * Jul. 12, 1994

[54] REHYDRATABLE PRODUCT AND METHOD OF PREPARATION THEREOF

[75] Inventors: Lindsay B. Llyod, West Jordan; Jon E. Beck; Tomasz J. Petelenz, both of Salt Lake City, all of Utah

[73] Assignee: Iomed, Inc., Salt Lake City, Utah

[*] Notice: The portion of the term of this patent subsequent to Aug. 17, 2010 has been disclaimed.

[21] Appl. No.: 38,798

[22] Filed: Mar. 29, 1993

Related U.S. Application Data

[63] Continuation-in-part of Ser. No. 627,714, Dec. 14, 1990, Pat. No. 5,236,412, which is a continuation-in-part of Ser. No. 383,939, Jul. 21, 1989, Pat. No. 5,087,242.

[51] Int. Cl.$^5$ .............................................. A61N 1/30
[52] U.S. Cl. ................................... 604/20; 607/151
[58] Field of Search ................. 604/20; 607/149, 151, 607/152

[56] References Cited

U.S. PATENT DOCUMENTS

| | | | |
|---|---|---|---|
| 4,362,165 | 12/1982 | Carmon et al. | 128/640 |
| 4,383,529 | 5/1983 | Webster | 128/802 |
| 4,416,274 | 11/1983 | Jacobsen et al. | 604/20 |
| 4,419,092 | 12/1983 | Jacobsen et al. | 128/803 |
| 4,474,570 | 10/1984 | Ariura et al. | 604/20 |
| 4,684,558 | 8/1987 | Keusch et al. | 428/40 |
| 4,702,732 | 10/1987 | Powers et al. | 128/803 |
| 4,708,149 | 11/1987 | Axelgaard et al. | 128/802 |
| 4,731,926 | 3/1988 | Sibalis | 604/20 |
| 4,747,819 | 5/1988 | Phipps et al. | 604/20 |
| 4,777,954 | 10/1988 | Keusch et al. | 128/640 |
| 4,842,577 | 6/1989 | Konno et al. | 604/20 |
| 4,867,166 | 9/1989 | Axelgaard et al. | 128/640 |
| 4,921,475 | 5/1990 | Sibalis | 604/20 |
| 4,989,607 | 2/1991 | Keusch et al. | 128/802 |
| 5,084,006 | 1/1992 | Lew et al. | 604/20 |
| 5,087,241 | 2/1992 | Mathiesen et al. | 604/20 |
| 5,087,242 | 2/1992 | Petelenz et al. | 604/20 |
| 5,158,537 | 10/1992 | Haak et al. | 604/20 |
| 5,236,412 | 8/1993 | Lloyd et al. | 604/20 |

FOREIGN PATENT DOCUMENTS

| | | | |
|---|---|---|---|
| 0058920 | 9/1982 | European Pat. Off. | 20/604 |
| 0299615 | 1/1989 | European Pat. Off. | 20/604 |
| 2184016 | 6/1987 | United Kingdom | 20/604 |

Primary Examiner—John D. Yasko
Assistant Examiner—Michael Rafa
Attorney, Agent, or Firm—Workman, Nydegger & Jensen

[57] ABSTRACT

A hydratable iontophoretic bioelectrode including a plurality of layers of material capable of absorbing and holding an ionized fluid when placed in contact with the fluid. In one embodiment, a layer of a highly crosslinked dry hydrogel is used with a second layer of a more lightly crosslinked dry hydrogel. When the lightly crosslinked hydrogel layer is located so as to be in contact with the skin during iontophoresis, the medicament ions will be concentrated next to the skin. When the more highly crosslinked layer is located next to the conductive member, the undesirable effects of hydrolysis or corrosion of the conductive member are lessened. In another embodiment, adjacent layers are maintained at least partially out of contact from one another so as to improve the rate of hydration by disposition between the layers of spacing elements such as sugar or other dissolvable particles or cellulose or by forming a three dimensional pattern thereon.

14 Claims, 4 Drawing Sheets

REHYDRATABLE PRODUCT AND METHOD OF PREPARATION THEREOF

BACKGROUND OF THE INVENTION

This is a continuation-in-part application of application Ser. No. 07/627,714, filed Dec. 14, 1990, now U.S. Pat. No. 5,236,412 which was a continuation-in-part of said Ser. No. 07/383,939, now U.S. Pat. No. 5,087,242, filed Jul. 21, 1989 and issued Feb. 11, 1992.

This invention relates to a rehydratable product or membrane especially suitable for use in an iontophoretic bioelectrode system, and to a method of preparing the rehydratable membrane.

Iontophoretic bioelectrodes, used in place of hypodermic needles to inject medications into a person's skin or tissue, typically include a pouch or similar enclosure formed with a wettable barrier or a microporous membrane on one side thereof. See, for example, U.S. Pat. Nos. 4,250,878; 4,419,092; and 4,477,971. A medication solution containing ions to be delivered into the person's skin or tissue is injected into the pouch by means of a hypodermic needle, syringe, etc. When the wettable barrier or membrane is placed against a person's skin and an electric current is supplied to the solution, the ions are caused to migrate from the solution through the wettable barrier or membrane, and into the skin.

A second bioelectrode is used in conjunction with the above-described iontophoretic bioelectrode, but need not include a solution of medicament ions. Rather, the second bioelectrode need only include an element for making contact with the person's skin or tissue (generally in close proximity to the iontophoretic bioelectrode), such as a wettable barrier or membrane containing nontoxic electrolyte for allowing migration of current (of opposite polarity to that of the current supplied to the iontophoretic bioelectrode) between the person's skin or tissue through the contact element to a second current source.

For the iontophoretic bioelectrode described earlier, barriers or membranes are required to retain the solution in the pouch while allowing ions to migrate therethrough. However, such barriers or membranes also inhibit wetting of the skin and thus inhibit the migration of ions to a certain extent, at least as compared to a situation where the solution would be in direct contact with the skin. Also, because of the use of a pouch or similar enclosure to contain the medication solution, a mechanism or structure on the enclosure is necessary for allowing the injection thereinto of the solution. Such structure has typically included some type of orifice containing a plug into which a hypodermic needle or syringe tube may be inserted to allow delivery of the solution through the orifice into the interior of the enclosure, while preventing the outflow of the solution after it has been injected into the enclosure. The requirement of such solution receiving mechanism or enclosure, of course, increases the cost of the bioelectrode and gives rise to potential leakage locations.

In U.S. Pat. No. 5,087,242, and in copending application Ser. No. 07/645,028 filed Jan. 23, 1991, the disclosures of which are both incorporated herein by reference, hydratable bioelectrodes are disclosed in which the need for special solution receiving structure or mechanisms is obviated. Such bioelectrodes include a layer of material for absorbing and holding aqueous solutions when placed in contact therewith, a conductive element disposed in close proximity to the layer of material for receiving an electrical charge to thereby cause ions in the fluid to move to and from the layer of material toward or away from the conductive element, and a support base on which the layer of material and conductive element are mounted. The layer of material may comprise a polymer, a matrix of fibers impregnated or interwoven with a hydratable polymer, or similar ion solution absorbing material. The aforesaid bioelectrode structures provide a simple, inexpensive and easy to use iontophoretic delivery mechanism.

Although U.S. Pat. No. 5,087,242 and the copending parent applications, Ser. Nos. 07/627,714 and 07/645,028 disclose useful methods and apparatus for constructing hydratable bioelectrodes, additional enhancements could be made to the previously disclosed technology in order to prepare hydratable bioelectrodes suitable for use in the practice of iontophoresis.

SUMMARY OF THE INVENTION

It is an object of the invention to provide methods and structures for simple, inexpensive, and skin contour conformable iontophoretic bioelectrodes.

It is also an object of the invention to provide dry iontophoretic bioelectrodes which are capable of efficiently absorbing and holding an aqueous solution when placed in contact therewith.

It is another object of the present invention to concentrate drug in the bioelectrode in a region next to the patient's skin.

Yet another object of the present invention is to provide a bioelectrode more resistant to undesirable effects from formation of electrolysis products or conductive element corrosion products.

It is an additional object of the invention to provide iontophoretic bioelectrodes which may be constructed using conventional equipment.

The above and other objects of the invention are realized in a specific illustrative embodiment of a hydratable bioelectrode for delivering ionized medicament into the skin or tissue of a person or animal. The bioelectrode includes a dry hydratable element for absorbing ionized medicament in aqueous solution when placed in contact therewith, a conductive element mounted in adjacent to the hydratable element for receiving an electrical current to thereby produce an electrical field and cause ionized medicament to move from the hydratable element into the skin or tissue on which the bioelectrode is placed, and means for securing the hydratable element to the conductive element.

In accordance with one aspect of the invention, the hydratable element includes means for separating adjacent sheets of dry hydrogel (sometimes hereafter referred to as "DH") which comprises separation elements such as granules or fibers disposed between each pair of adjacent sheets of DH, with such granules or fibers comprising, for example, sugar crystals, cellulose fibers, etc.

In accordance with another aspect of the invention, the sheets of DH are formed to be relatively stiff to enable maintaining the sheets apart from one another by the separation elements so that when the sheets are exposed to medicament for absorption thereof, there is a greater surface area of the DH sheets in contact with the medicament and thus there is a more rapid complete and uniform absorption. Another alternative is to form fluid channels between the sheets, such as by forming three dimensional patterns on the sheets.

Another embodiment of the invention involves the use of layers of DH's having different aqueous solution absorption properties. Hydrophilic polymers may be crosslinked to different degrees. Crosslinking binds the polymer molecules into a network which can swell with aqueous solution without completely dispersing. An insoluble hydrogel is formed. The degree of swelling and porosity of the hydrogel depends on the number of crosslinks. A highly crosslinked hydrophilic polymer network (sometimes hereafter referred to as "HCDH" for highly crosslinked dry hydrogel) swells to a lesser extent in aqueous solution and is less porous to migrating ionic species than a lightly crosslinked network ("LCDH") of the same polymer. Thus, migration rates of species contained in the DHs can be controlled through adjusting the degree of crosslinking within the DH.

A layer of LCDH may be placed in contact with the conductive element, and a layer of HCDH affixed to the other side thereof so that the less hydrophilic polymer will be placed against the patient's or animal's skin or other tissue during use. This configuration will lessen the impact of undesirable hydrolysis products or corrosion products associated with the conductive member. Alternatively, the conductive member may be placed in contact with the HCDH, so that the highly hydrophilic polymer is placed in contact with the skin. This configuration concentrates medicament in the region next to the skin.

BRIEF DESCRIPTION OF THE DRAWINGS

The above and other objects, features and advantages of the invention will become apparent from a consideration of the following detailed description presented in connection with then accompanying drawings in which:

FIG. 1 (comprised of FIGS. 1A and 1B) shows flow diagram of the method of constructing hydratable bioelectrodes in accordance with the principles of the present invention.

DETAILED DESCRIPTION

Figure 1A:
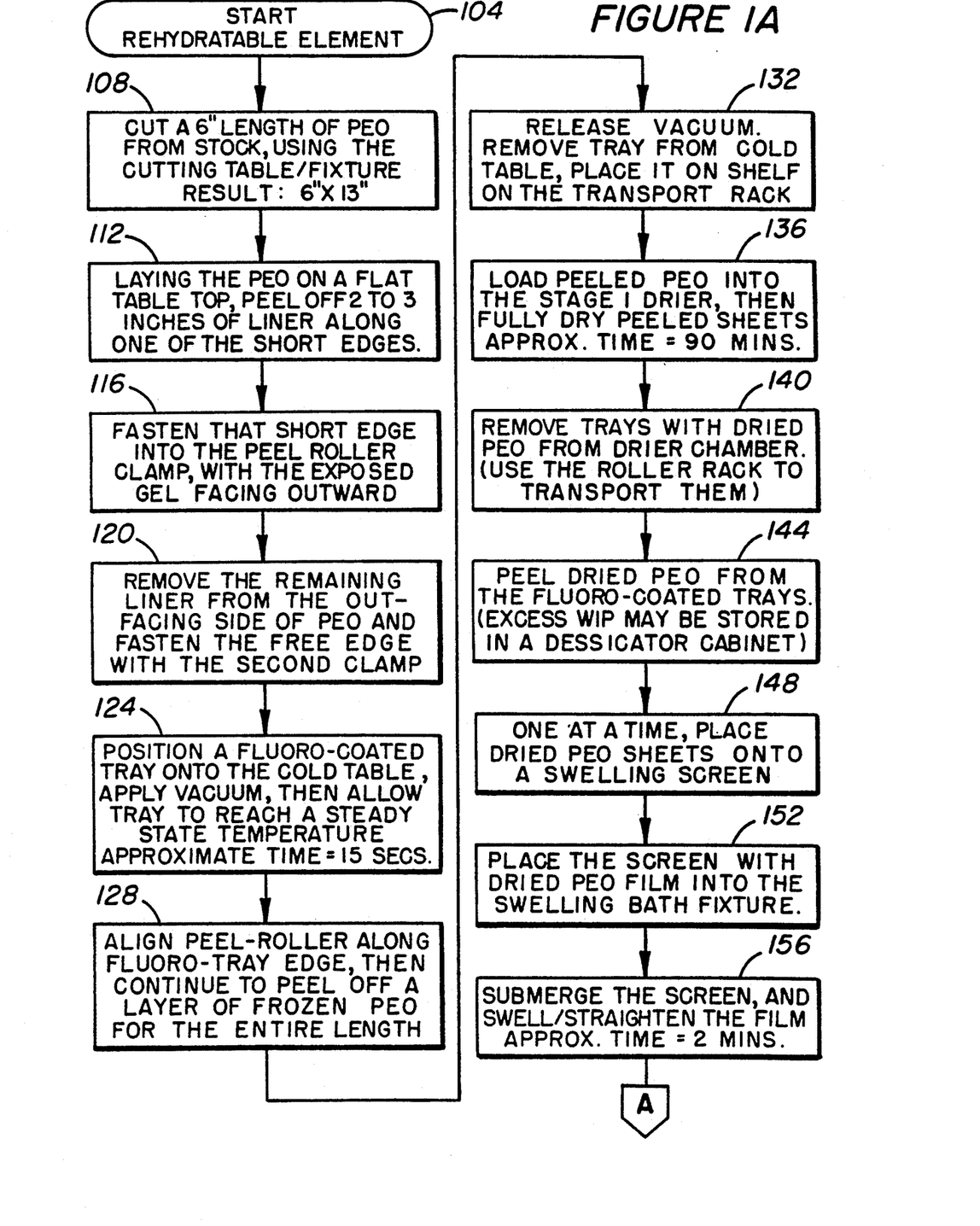
Figure 1B:
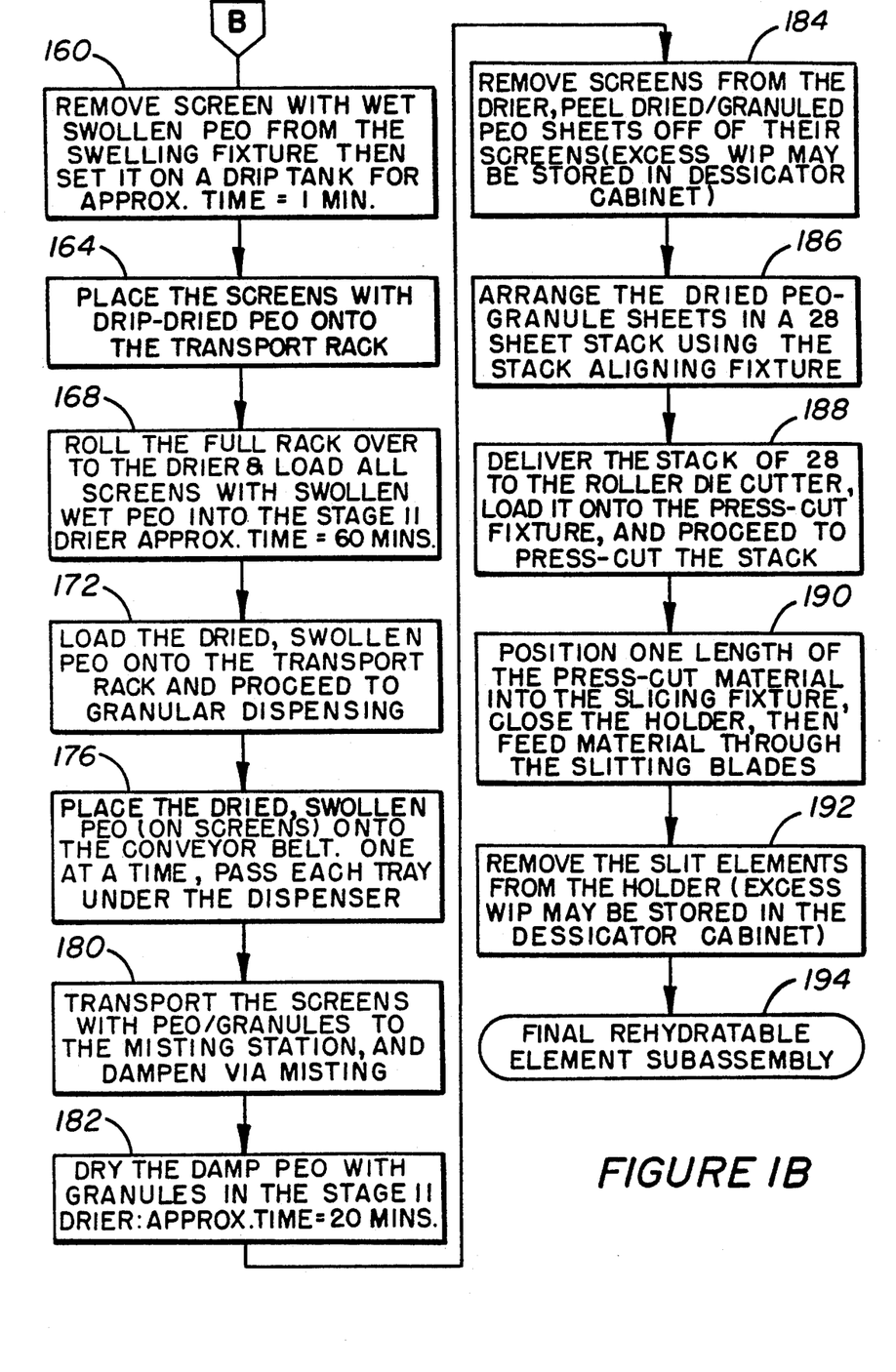

FIG. 1 is a flow chart showing the steps of one embodiment of a presently preferred method of producing a hydratable bioelectrode in accordance with the present invention. An exemplary starting material for the method of FIG. 1 is shown in cross section in FIG. 2 to include a mass of gel material 204 sandwiched between two layers of liner material 208 and 212 made, for example, of plastic. A sheet of scrim (mesh material) 216 is disposed in the gel mass generally midway between the two liners 208 and 212. The starting material illustrated in FIG. 2 might illustratively be an inert hydrogel identified as STD-1 or WD-1 which are the products of Nepera, Inc. used as skin dressing for wounds, burns, etc. The particular hydrogels which are presently preferred constitute a polyethylene oxide polymer which is crosslinked, for example, using e-beam radiation, by chemical means, or by other strong radiation such as gamma rays.

However, the starting material could also be another hydrophilic material, such as wet or dry, crosslinked sheets of polyvinyl alcohol, PVA, poly-N-vinyl pyrrolidone or other substituted pyrrolidones, PVP, polyacrylamides such as poly-Nisopropyl acrylamide, NIPPAm, polyhydroxyethyl methacrylate, PHEMA or hydrophilic substituted HEMAs, polysaccharides such as agarose, hydroxy cellulose, HEC, hydroxyethyl methyl cellulose, HPMC, hydroxypropyl cellulose, carboxyethyl cellulose, HPC, hydroxypropyl methyl cellulose, dextrans, modified starches, modified collagens, xanthan gum, modified natural gums, partially neutralized polyelectrolytes such as polyacrylic acid, polyimides, and alginates. It might also be suitable in some circumstances to use copolymer mixtures of the foregoing. However, the preferred polymers are non-ionic or non-electrolyte hydrophilic polymers or copolymers such as PEO, PVP, PAAm, and HEC because these do not contain large numbers of ionizable moieties which would otherwise compete as charge carriers with the drug to be iontophoretically administered.

Figure 2:
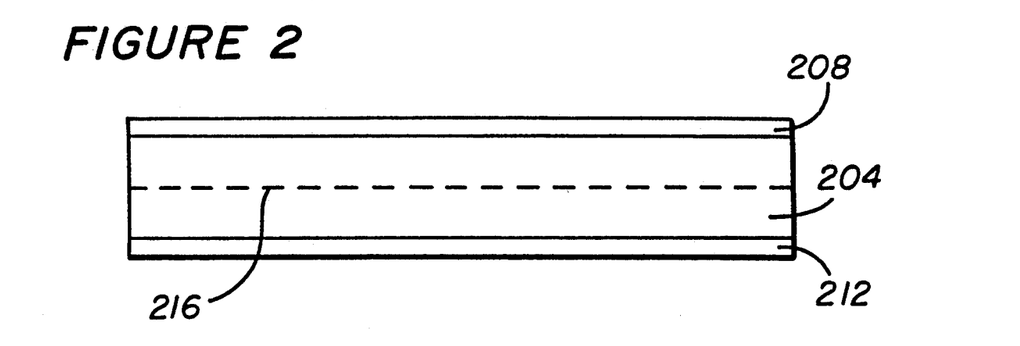
FIG. 2 shows a side, cross-sectional view of a starting product for use in the method illustrated in FIG. 1.

Referring now to FIG. 1, the first step of the method or process of producing a hydratable bioelectrode is to provide a starting material such as that shown in FIG. 2. From such a stock piece of material, a strip of, for example, six inches by thirteen inches is cut out in a conventional fashion (step 108 of FIG. 1) and then laid flat on a table to allow peeling off of the top liner sheet 208 (steps 112, 116 and 120 of FIG. 1). (The term "PEO" used in some of the steps of FIG. 1 means "polyethylene oxide" and the term "WIP" means "work in process".) Although the steps shown in boxes 112, 116 and 120 of FIG. 1 are rather specific for peeling off the top liner 208 of the starting material of FIG. 2, it should be understood that any of a variety of approaches could be taken for removing the liner; further starting material without any liner to begin with could be provided and then, of course, steps 112, 116 and 120 would not be necessary.

After step 120 of FIG. 1, the gel mass or layer 204 and remaining liner 212 are wound about a roller device so that the gel layer 204 faces outwardly. The next step in the process is to place a fluoroplastic-coated tray onto a cold table to cool the tray, with the tray being held in place by a vacuum in a conventional fashion. When the tray reaches a steady state temperature of, for example, eighteen degrees Fahrenheit (a temperature below the freezing point of the gel layer), as indicated in step 124, the roller, with gel layer wound thereabout, is aligned along one edge of the cooled tray (step 128) and rolled at a predetermined, controlled rate to cause the outward facing or upper layer of the gel material 204 to freeze and hold onto the tray so that as the roller continues to roll, the thin upper layer (down to the scrim 216) is peeled away from the remainder of the gel on the roller and frozen onto the tray. If no scrim 216 were present in the gel mass 204, the tray temperature, and rate of rolling the roller, would determine the thickness of the layer of gel which is frozen to the tray and peeled from the roller. A layer of gel is now disposed on the tray and another gel layer sandwiched between the scrim 216 and liner 212 remains on the roller.

With the layer of gel on the tray, the tray is placed in a convection drying chamber (step 136) which has been heated to about 55° centigrade. The purpose of this is to dry the gel layer at a temperature which will not cause degradation of the gel (typically about 60° centigrade). The dried hydrogel (DH) layer is then removed from the tray and placed onto a screen and clamped to maintain the planarity of the layer (steps 144 and 148), and the screen is then immersed in a "swelling" solution of water (step 152) containing a stiffening agent such as sugar, for example, 50 grams per liter. The purpose of the stiffening agent will be discussed later. The screen on which the DH layer is placed may illustratively be a perforated fluoro-coated metal sheet, with another screen on top to maintain the flatness of the gel layer.

The screen with DH layer remains submerged in the swelling solution for a sufficient time to allow the layer to absorb solution, swell and expand laterally (step 156). The screen with swollen gel layer is then removed from the swelling solution, blotted dry (step 160) and after sufficient blotting, the screen with gel layer is again placed in the convection drying chamber to further dry the gel layer (step 168). After swelling and the final step of drying, the DH layer will be formed into a sheet having substantially the same length and width dimensions, but the thickness will have decreased substantially from when wet.

In the next stage of the process, granules or fibers are distributed onto the DH sheet to serve as spacers to maintain apart, to the extent possible, adjacent DH sheets which will later be used to form a stack of DH sheets. Individual DH sheets will be fairly stiff, as a result of immersion thereof in the swelling solution with stiffening agent, and so the distribution of granules or fibers, such as sugar, over the DH sheets will serve as spacers when the DH sheets are placed in a stack. Other materials which will form granules useful in connection with the present invention include salt crystals, cellulose, starch, crosslinked particles of polymers, insoluble polymer beads, grains, or ion exchange resins.

One way of distributing the granules or fibers onto the DH sheet is to place the DH sheet onto a conveyor belt and pass it under a granule/fiber dispenser (step 176). It is desired to maintain individual DH sheets separated when in a stack so that when hydrated with iontophoretic medicament, the medicament will be allowed to flow between the sheets and thus be more rapidly and uniformly absorbed by the ultimate gel sheet stack.

In step 180, a fine water vapor or mist is applied to the DH sheet simply to better hold the granules or fibers on the DH sheet surface. The water vapor or mist partially dissolves granules such as sugar causing them to "stick" onto the DH sheet. It is important that too much water vapor or mist not be used so that the granules are not dissolved completely, since, of course, they would then not serve to maintain the DH sheet separated from adjacent sheets.

After securing the granules of fibers onto the DH sheet, the DH sheet is removed from the screen (step 184) and then arranged in a stack with other DH sheets, for a total, for example, of 28 layers (step 186). A sufficient number of layers of DH sheets are included in a stack so that when the DH sheets are incorporated into a bioelectrode such as that shown in FIG. 3, a conductive member 304 which receives electrical current from a current source 308 will not burn the skin or tissue of a person against which the bioelectrode is placed. On the other hand, if too many layers are used to form the stack, then assembly may become too costly.

After the sheets are formed into a stack, the stack is press-cut by a roller press (step 188) which both cuts the stack lengthwise, for example, and also crimps the resulting adjacent edges so cut, although alternative means for binding the layers together could be used, such as an adhesive (e.g., cyanoacrylate), stitches, staples, or welds.

Figure 3:
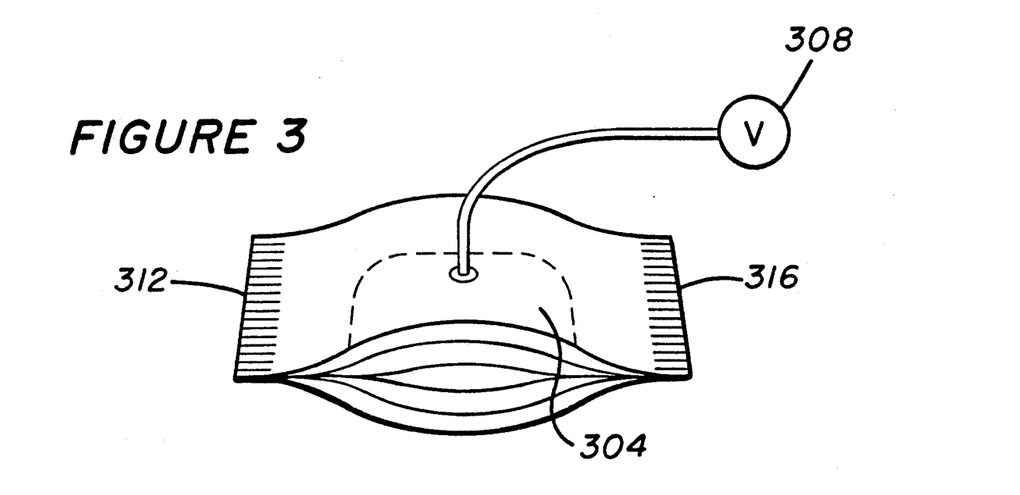
FIG. 3 is an end, cross-sectional view of an iontophoretic bioelectrode made in accordance with the principles of the present invention.

FIG. 3 shows opposite edges 312 and 316 of a DH sheet stack which have been crimped and cut. Note that the edges which are crimped are much thinner than the center portion of the stack which, of course, has not been crimped. In step 190, the stack is then cut perpendicularly to the press-cut made in step 188 to thereby provide plurality of individual stacks of DH sheets, each of which may then be incorporated into a bioelectrode structure such as that shown in FIG. 3 (step 194 or FIG. 1).

In the manner described, a simple iontophoretic bioelectrode is provided in which the ionized medicament may be absorbed into a stack of DH sheets which are part of the bioelectrode. The hydrated sheets may then be placed in direct contact with the skin or tissue of a person or animal for administering the medicament and because the gel sheets are in direct contact, improved wetting of the skin or tissue, and thus more efficient delivery of the ions, is achieved.

Figure 4:
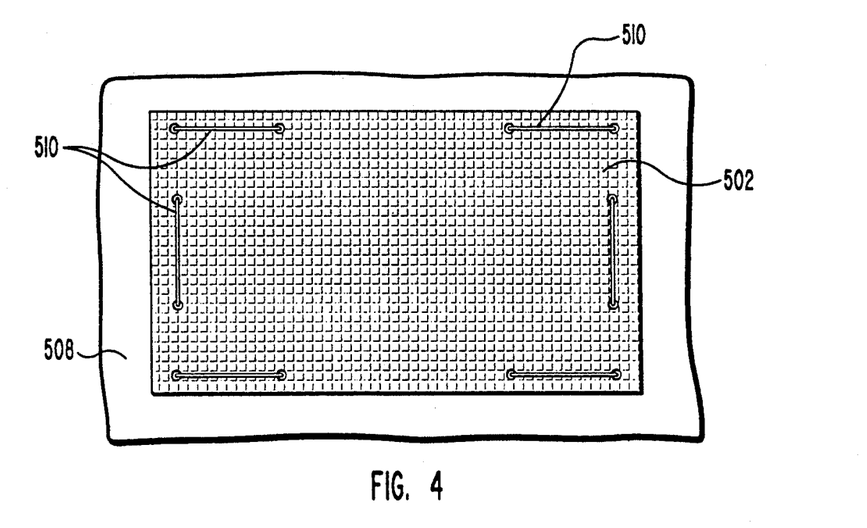
FIG. 4 is a plan view of one presently preferred electrode of the invention, also illustrating a sheet of hydrogel in accordance with the present invention on the surface of which has been formed a three dimensional pattern which will cause separations between adjacent sheets when stacked.

In place of granules or fibers as described above, other means for separating adjacent sheets of DH may be used. For example, it is possible to press, form, emboss, machine or otherwise treat each sheet so as to contain a threedimensional pattern. When stacked, such three dimensional patterns cause adjacent sheets to lie in a spaced relationship to one another, thereby providing for rapid and complete hydration when a medicament solution is applied prior to use of the bioelectrode. FIG. 4 is a plan view which illustrates one three dimensional pattern which might be formed on the surface of DH sheets to assist in rapid hydration.

Other modifications may be made to solve other problems which might exist in a particular situation. For example, it is possible to utilize a different type of hydrogel in two or more adjacent layers or similar hydrogels having different hydrophilic properties due to differing degrees of crosslinking. One such construction could advantageously comprise a layer of one or more LCDH sheets of polyethylene oxide (PEO). This layer of LCDH could be secured to a layer of one or more HCDH sheets of PEO, PHEMA, or any of the other hydrophilic polymers listed above.

Figure 5:
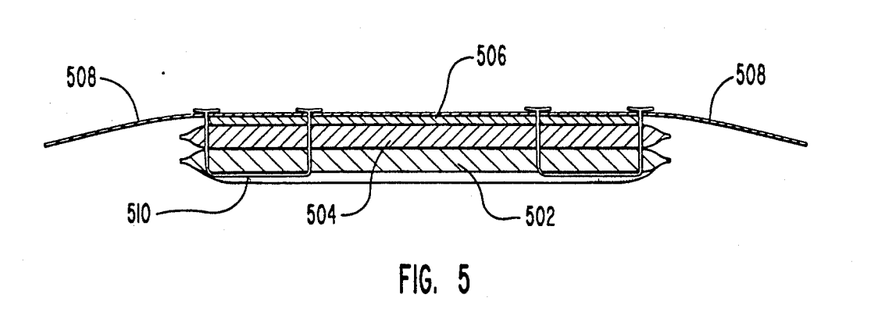
FIG. 5 is a side, cross-sectional view of a bioelectrode similar to that of FIG. 4, formed of two layers of polymer having different aqueous swelling characteristics.

One embodiment using layers of differing gel structures is shown in FIG. 5. There, a hydratable element includes a layer 502 of a PEO-based LCDH, and a layer 504 of PHEMAbased HCDH. Layer 502 is situated so as to be placed against a patient's skin during use of the bioelectrode, while layer 504 is situated adjacent to and in contact with a conductive element 506. An adhesive member 508 is advantageously applied over the entire assembly in order to serve as a means for affixing the electrode to a patient. Stitches 510 serve as means for securing the hydratable element to the conductive element. Upon application of a medicament solution, the electrode construction of FIG. 5 has the advantage of concentrating drug in the region closest to the patient's skin. Not only does this limit the total amount of drug necessary, but also assists in even distribution and delivery of drug.

Figure 6:
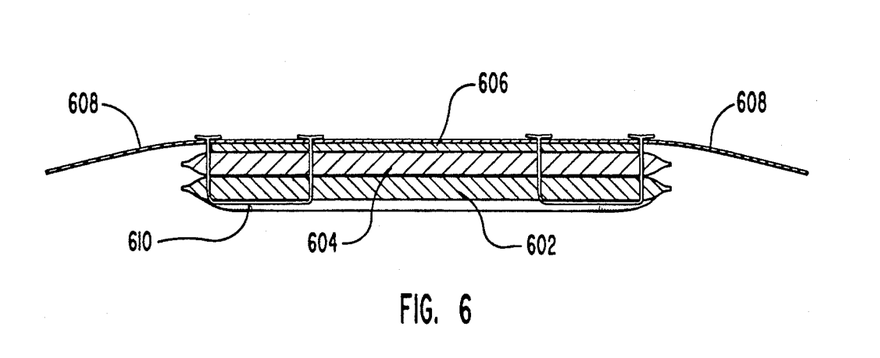
FIG. 6 is a side, cross-sectional view of a bioelectrode similar to that of FIG. 5, but with the order of layers reversed.

Alternatively, the less crosslinked layer might be situated so as to be placed against the patient's skin, and the more highly crosslinked layer situated so as to contact the conductive element, as shown in FIG. 6, where layer 602 of LCDH is shown adjacent to conductive member 606, and layer 604 of a HCDH is shown in position for affixation to a patient's skin. Again, an adhesive member 608 serves as a means for affixing the electrode to a patient, and stitches 610 serve as means for securing the hydratable element to the conductive element. The construction of FIG. 6 would be useful, for example, in situations where undesirable electrolysis products (H+ or OH−) or conductive element corrosion products are formed, by slowing the passage of these unwanted products from the region next to the conductive element to the patient's skin due to a decrease in diffusion coefficient when moving from the region having a looser mesh (lightly crosslinked PEO) to the tighter mesh of the more highly crosslinked gel layers.

Another means for controlling pH changes or removing unwanted ionic species is by incorporating a suitable anion or cation exchange resin, or combination of both anion and cation exchange resins, into the hydrogel. Examples of useful anion exchange resins would utilize amino or quaternary amino groups. Examples of useful cation exchange resins would utilize carboxy or sulfoxy groups. Materials such as PAA, polyethylimine, dextrans, natural gums such as xanthan or alginate, or collagen could each be used in varying applications.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A bioelectrode for iontophoretically delivering medicament into the skin or tissue of a person or animal comprising:
   a hydratable element for absorbing ionized medicament solution when placed in contact therewith, said hydratable element comprising a horizontally positioned layer of a lightly crosslinked dry hydrogel stacked with a horizontally positioned layer of a highly crosslinked dry hydrogel;
   a conductive element mounted adjacent to the hydratable element for receiving an electrical current to produce an electrical field and cause ionized medicament to move from the hydratable element into the skin or tissue on which the bioelectrode is placed; and
   means for securing the hydratable element to the conductive element.

2. A bioelectrode as defined in claim 1, wherein the layer of lightly crosslinked dry hydrogel comprises one or more sheets of lightly crosslinked dry hydrogel, and wherein the layer of highly crosslinked dry hydrogel comprises one or more sheets of highly crosslinked dry hydrogel.

3. A bioelectrode as defined in claim 1, further comprising separating means for spacing adjacent sheets of polymer apart so that when hydrated with ionized medicament solution, the medicament solution is rapidly absorbed in the hydratable element.

4. A bioelectrode as defined in claim 3, wherein the separating means comprises granules or fibers.

5. A bioelectrode as defined in claim 4, wherein the granules or fibers comprise sugar crystals, starch, crosslinked polymer, insoluble polymer beads, grains, or ion exchange resin.

6. A bioelectrode as defined in claim 3 wherein the separating means has a raised pattern formed on the surface of the sheets of polymer so that when stacked, adjacent sheets lie in a spaced relationship to one another.

7. A bioelectrode as defined in claim 1, wherein the conductive element is mounted adjacent to the layer of lightly crosslinked dry hydrogel, and the layer of highly crosslinked dry hydrogel is mounted so as to be disposed during use against the skin or tissue of the person or animal into which medicament is to be delivered.

8. A bioelectrode as defined in claim 1, wherein the conductive element is mounted adjacent to the layer of highly crosslinked dry hydrogel, and the layer of lightly crosslinked dry hydrogel is mounted so as to be disposed during use against the skin or tissue of the person or animal into which medicament is to be delivered.

9. A bioelectrode as defined in claim 1, wherein the hydratable element includes one or more additional layers of dry hydrogel, said one or more layers being positioned horizontally in stacked relationship with the remaining horizontal layers of the hydratable element.

10. A bioelectrode as defined in claim 1, wherein the lightly crosslinked dry hydrogel is lightly crosslinked polyethylene oxide and the highly crosslinked dry hydrogel is highly crosslinked PHEMA.

11. A bioelectrode as defined in claim 1, further including ion exchange resin or polymer incorporated within the hydratable element.

12. A bioelectrode as defined in claim 11, wherein the ion exchange resin or polymer is incorporated into the layer of dry hydrogel which is adjacent to the conductive element.

13. A bioelectrode for iontophoretically delivering medicament into the skin or tissue of a person or animal comprising:
    a hydratable element for absorbing ionized medicament solution when placed in contact therewith, said hydratable element comprising a stack of at least two horizontally positioned sheets of a crosslinked hydrophilic polymer capable of absorbing medicament solution;
    a conductive element mounted adjacent to the hydratable element for receiving an electrical current to produce an electrical field and cause ionized medicament to move from the hydratable element into the skin or tissue on which thte bioelectrode is placed;
    means for securing the hydratable element to the conductive element;
    separating means for maintaining adjacent sheets at least partially separated in order to assist rapid hydration upon addition of medicament solution, said separating means comprising a raised pattern formed on the surface of said sheets so taht when stacked, adjacent sheets lie in a spaced relationship to one another; and
    means for securing the sheets in the stack.

14. A bioelectrode for iontophoretically delivering medicament into the skin or tissue of a person or animal comprising:
- a hydratable element for absorbing ionized medicament solution when placed in contact therewith, said hydratable element comprising a stack of at least two horizontally positioned sheets of a cross-linked hydrophilic polymer capable of absorbing medicament solution;
- a conductive element mounted adjacent to the hydratable element for receiving an electrical current to produce an electrical field and cause ionized medicament to move from the hydratable element into the skin or tissue on which the bioelectrode is placed;
- means for securing the hydratable element to the conductive element;
- separating means for maintaining adjacent sheets at least partially separated in order to assist rapid hydration upon addition of medicament solution, said separating means comprising starch, cross-linked polymer, insoluble polymer beads, grains or ion exchange resin; and
- means for securing the sheets in the stack.

* * * * *

UNITED STATES PATENT AND TRADEMARK OFFICE
CERTIFICATE OF CORRECTION

PATENT NO. : 5,328,455
DATED : July 12, 1994
INVENTOR(S) : LINDSAY B. LLOYD et al.

It is certified that error appears in the above-indentified patent and that said Letters Patent is hereby corrected as shown below:

Title page, column 1, item [19], "Llyod et al." should be —Lloyd et al.—

Title page, column 1, item [75], "Lindsay B. Llyod" should be —Lindsay B. Lloyd—

Column 3, line 37, after "shows" insert —a—

Column 6, line 36, "threedimensional" should be —three-dimensional—

Column 8, line 65, "taht" should be —that—

Signed and Sealed this

Twenty-eighth Day of November 1995

Attest:

BRUCE LEHMAN

*Attesting Officer*   *Commissioner of Patents and Trademarks*